(12) United States Patent
Bretschneider et al.

(10) Patent No.: US 6,894,074 B2
(45) Date of Patent: May 17, 2005

(54) SYNERGISTIC INSECTICIDAL MIXTURES

(75) Inventors: Thomas Bretschneider, Lohmar (DE);
Reiner Fischer, Monheim (DE);
Christoph Erdelen, Leichlingen (DE);
Ernst Brück, Bergisch Gladbach (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 10/673,870

(22) Filed: Sep. 29, 2003

(65) Prior Publication Data

US 2004/0082650 A1 Apr. 29, 2004

Related U.S. Application Data

(62) Division of application No. 09/937,239, filed as application No. PCT/EP00/02238 on Mar. 14, 2000, now Pat. No. 6,716,874.

(30) Foreign Application Priority Data

Mar. 24, 1999 (DE) .......................................... 199 13 174

(51) Int. Cl.$^7$ .......................... A01N 43/08; A01N 43/12
(52) U.S. Cl. ...................... 514/462; 514/461; 514/463; 514/464; 514/465; 514/466; 514/467; 514/468; 514/469; 514/470; 514/471; 514/472; 514/473; 514/474
(58) Field of Search ................................. 514/461–474

(56) References Cited

U.S. PATENT DOCUMENTS

| 35,811 A | 5/1862 | Shiokawa et al. ........... 514/357 |
|---|---|---|
| 4,511,350 A | 4/1985 | Romanauskas ............... 494/82 |
| 4,531,002 A | 7/1985 | Harris .......................... 544/54 |
| 4,590,272 A | 5/1986 | Shiokawa et al. ........... 544/335 |
| 4,606,862 A | 8/1986 | Harris ...................... 260/402.5 |
| 4,647,570 A | 3/1987 | Shiokawa et al. ........... 514/341 |
| 4,680,294 A | 7/1987 | Shiokawa et al. ........... 514/256 |
| 4,687,845 A | 8/1987 | Hollowood et al. ........... 544/54 |
| 4,742,060 A | 5/1988 | Shiokawa et al. ........... 514/252 |
| 4,772,247 A | 9/1988 | Stockton ......................... 474/8 |
| 4,772,620 A | 9/1988 | Shiokawa et al. ........... 514/341 |
| 4,803,277 A | 2/1989 | Shiokawa et al. ........... 514/332 |
| 4,806,553 A | 2/1989 | Shiokawa et al. ........... 514/332 |
| 4,812,454 A | 3/1989 | Shiokawa et al. ........... 514/256 |
| 4,812,571 A | 3/1989 | Shiokawa et al. ........... 546/296 |
| 4,845,106 A | 7/1989 | Shiokawa et al. ........... 514/342 |
| 4,849,432 A | 7/1989 | Shiokawa et al. ........... 514/341 |
| 4,882,344 A | 11/1989 | Shiokawa et al. ........... 514/342 |
| 4,914,113 A | 4/1990 | Shiokawa et al. ........... 514/333 |
| 4,918,086 A | 4/1990 | Gsell ........................... 514/351 |
| 4,918,088 A | 4/1990 | Gsell ........................... 514/357 |
| 4,948,798 A | 8/1990 | Gsell ........................... 514/275 |
| 4,963,572 A | 10/1990 | Gsell ........................... 514/357 |
| 4,963,574 A | 10/1990 | Bachmann et al. .......... 514/357 |
| 4,988,712 A | 1/1991 | Shiokawa et al. ........... 514/340 |
| 5,001,138 A | 3/1991 | Shiokawa et al. ........... 514/342 |
| 5,032,589 A | 7/1991 | Shiokawa et al. ........... 514/245 |
| 5,034,404 A | 7/1991 | Uneme et al. ............... 514/365 |
| 5,034,524 A | 7/1991 | Shiokawa et al. ........... 544/124 |
| 5,039,686 A | 8/1991 | Davies et al. | |
| 5,049,571 A | 9/1991 | Gsell ........................... 514/345 |
| 5,051,434 A | 9/1991 | Kozo et al. .................. 514/357 |
| 5,054,194 A | 10/1991 | Pollock ......................... 29/840 |
| 5,063,236 A | 11/1991 | Gsell ........................... 514/318 |
| 5,066,808 A | 11/1991 | Shiokawa et al. ....... 514/231.5 |
| 5,084,467 A | 1/1992 | Shiokawa et al. ........... 514/357 |

(Continued)

FOREIGN PATENT DOCUMENTS

| CA | 2052731 | 4/1992 |
|---|---|---|
| DE | 36 39 877 | 5/1988 |
| DE | 37 12 307 | 10/1988 |
| DE | 42 16 814 | 1/1993 |
| DE | 195 19 007 | 11/1996 |
| JP | 63287764 | 11/1988 |
| JP | 63307857 | 12/1988 |
| JP | 2-207083 | 8/1990 |
| JP | 3220176 | 9/1991 |
| JP | 3246283 | 11/1991 |
| JP | 3255072 | 11/1991 |
| JP | 3279359 | 12/1991 |
| JP | 4009371 | 1/1992 |
| JP | 5178883 | 7/1993 |
| JP | 7173157 | 7/1995 |
| JP | 8291171 | 11/1996 |
| WO | 91/17859 | 11/1991 |

OTHER PUBLICATIONS

CABA Abstract, accession No. 1999:29730 (entered into the database on Mar. 10, 1999).*
Chem. Inc., 37, (month unavailable), 1985, pp. 730–731, H. R. Ungerer, "Schiffsfarben—eine Spezialität der seenahen Lackindustrie".
Weeds, 15, (month unavailable), 1967, pp. 20–22, S. R. Colby, "Calculating Synergistic and Antagonistic Responses of Herbicide Combinations".

Primary Examiner—John Pak
(74) Attorney, Agent, or Firm—Richard E. L. Henderson; Raymond J. Harmuth

(57) ABSTRACT

The invention relates to insecticidal mixtures comprising compounds of the formula (I)

(I)

[chemical structure]

in which X', Y', Z', n, G', A' and B' are as defined above and agonists and/or antagonists of nicotinic acetylcholine receptors, for protecting plants against attack by pests.

6 Claims, No Drawings

U.S. PATENT DOCUMENTS

| | | | |
|---|---|---|---|
| 5,166,164 A | 11/1992 | Nanjo et al. | 514/357 |
| 5,175,301 A | 12/1992 | Minamida et al. | 546/272 |
| 5,192,778 A | 3/1993 | Kodaka et al. | 514/341 |
| 5,204,359 A | 4/1993 | Shiokawa et al. | 514/332 |
| 5,204,360 A | 4/1993 | Shiokawa et al. | 514/342 |
| 5,214,152 A | 5/1993 | Minamida et al. | 548/181 |
| 5,238,949 A | 8/1993 | Shiokawa et al. | 514/327 |
| 5,256,679 A | 10/1993 | Minamida et al. | 514/357 |
| 5,262,383 A * | 11/1993 | Fischer et al. | 504/195 |
| 5,264,584 A | 11/1993 | Kodaka et al. | 548/332.5 |
| 5,280,123 A | 1/1994 | Nanjo et al. | 548/111 |
| 5,298,507 A | 3/1994 | Shiokawa et al. | 514/256 |
| 5,384,324 A | 1/1995 | Shiokawa et al. | 514/365 |
| 5,405,961 A | 4/1995 | Nanjo et al. | 544/243 |
| 5,428,032 A | 6/1995 | Shiokawa et al. | 514/226.8 |
| 5,434,181 A | 7/1995 | Kodaka et al. | 514/471 |
| 5,461,167 A | 10/1995 | Shiokawa et al. | 548/202 |
| 5,489,603 A | 2/1996 | Uneme et al. | 514/365 |
| 5,532,365 A | 7/1996 | Kodaka et al. | 544/212 |
| 5,580,889 A | 12/1996 | Shiokawa et al. | 514/343 |
| 5,614,527 A | 3/1997 | Kinoshita et al. | 514/256 |
| 5,633,375 A | 5/1997 | Uneme et al. | 544/336 |
| 5,696,256 A | 12/1997 | Kando et al. | 540/463 |
| 5,719,146 A | 2/1998 | Shiokawa et al. | 514/229.2 |
| 5,750,704 A | 5/1998 | Shiokawa et al. | 546/275.1 |
| 5,849,768 A | 12/1998 | Minamida et al. | 514/357 |
| 5,852,012 A | 12/1998 | Maienfisch et al. | 514/229.2 |
| 5,935,981 A | 8/1999 | Minamida et al. | 514/365 |
| 6,022,871 A | 2/2000 | Maienfisch et al. | 514/229.2 |
| 6,022,967 A | 2/2000 | Shiokawa et al. | 544/298 |
| 6,124,297 A | 9/2000 | Minamida et al. | 514/255 |
| 6,160,126 A | 12/2000 | Kando et al. | 548/477 |
| 6,187,773 B1 | 2/2001 | Wu et al. | 514/245 |
| 6,232,309 B1 | 5/2001 | Shiokawa et al. | 514/222.5 |
| 6,297,374 B1 | 10/2001 | Shiokawa et al. | 544/55 |
| 6,344,453 B1 | 2/2002 | Shiokawa et al. | 514/223.8 |
| 6,376,487 B1 | 4/2002 | Maienfisch et al. | 514/229.2 |
| 6,407,248 B1 | 6/2002 | Minamida et al. | 546/331 |
| 6,762,183 B2 * | 7/2004 | Fischer et al. | 514/242 |
| 2001/0046994 A1 | 11/2001 | Wu et al. | 514/241 |

* cited by examiner

SYNERGISTIC INSECTICIDAL MIXTURES

This application is a divisional application of U.S. patent application Ser. No. 09/937,239, filed on Sep. 21, 2001, which is now U.S. Pat. No. 6,716,874, which is a 371 of PCT/EP00/02238, filed on Mar. 14, 2000. The PCT/EP00/02238 application claimed priority of German Patent Application Serial No. 199 13 174.0, filed on Mar. 24, 1999.

FIELD OF THE INVENTION

The present invention relates to novel active compound combinations which comprise, on the one hand, a known cyclic ketenol and, on the other hand, other known insecticidally active compounds, and which have very good insecticidal and acaricidal properties.

BACKGROUND OF THE INVENTION

It is already known that certain cyclic ketoenols can be used for controlling animal pests, such as insects and undesired acarids (cf. EP-A-528 156). The activity of these substances is good; however, it is sometimes unsatisfactory at low application rates.

Furthermore, it has also become known that agonists and antagonists of nicotinic acetylcholine receptors can be used for controlling insects.

SUMMARY OF THE INVENTION

The invention relates to insecticidal mixtures comprising cyclic ketoenols of the formula (I)

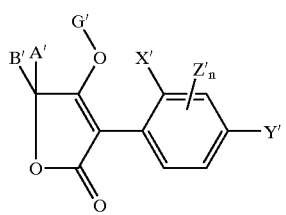

(I)

and agonists and/or antagonists of nicotinic acetylcholine receptors.

DETAILED DESCRIPTION

It has now been found that mixtures of cyclic ketoenols of the formula (I)

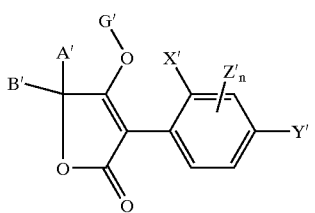

(I)

in which

X' represents $C_1$–$C_6$-alkyl, halogen, $C_1$–$C_6$-alkoxy or $C_1$–$C_3$-halogenoalkyl, Y' represents hydrogen, $C_1$–$C_6$-alkyl, halogen, $C_1$–$C_6$-alkoxy, $C_1$–$C_3$-halogenoalkyl, Z' represents $C_1$–$C_6$-alkyl, halogen, $C_1$–$C_6$-alkoxy, n represents a number from 0–3, A' and B' are identical or different and represent hydrogen or optionally halogen-substituted straight-chain or branched $C_1$–$C_{12}$-alkyl, $C_3$–$C_8$-alkenyl, $C_3$–$C_8$-alkinyl, $C_1$–$C_{10}$-alkoxy-$C_2$–$C_8$-alkyl, $C_1$–$C_8$-polyalkoxy-$C_2$–$C_8$-alkyl, $C_1$–$C_{10}$-alkylthio-$C_2$–$C_8$-alkyl, cycloalkyl having 3–8 ring atoms which may be interrupted by oxygen and/or sulphur, and optionally halogen-, $C_6$-alkyl-, $C_1$–$C_6$-halogenoalkyl-, $C_1$–$C_6$-alkoxy-, $C_1$–$C_6$-halogenoalkoxy-, nitro-substituted phenyl or phenyl-$C_1$–$C_6$-alkyl, or in which A' and B' together with the carbon atom to which they are attached represent a saturated or unsaturated 3- to 8-membered ring which is optionally interrupted by oxygen and/or sulphur and optionally substituted by halogen, $C_1$–$C_6$-alkyl, $C_1$–$C_6$-alkoxy, $C_1$–$C_4$-halogenoalkyl, $C_1$–$C_4$-halogenoalkoxy, $C_1$–$C_4$-alkylthio or optionally substituted phenyl or is optionally benzo-fused, G' represents hydrogen (a) or represents the groups

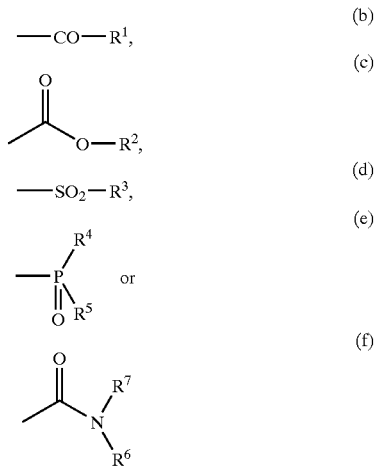

in which $R^1$ represents optionally halogen-substituted $C_1$–$C_{20}$-alkyl, $C_2$–$C_{20}$-alkenyl, $C_1$–$C_8$-alkoxy-$C_2$–$C_8$-alkyl, $C_1$–$C_8$-alkylthio-$C_2$–$C_8$-alkyl, $C_1$–$C_8$-polyalkoxy-$C_2$–$C_8$-alkyl or cycloalkyl having 3–8 ring atoms which may be interrupted by oxygen and/or sulphur atoms, represents optionally halogen-, nitro-, $C_1$–$C_6$-alkyl-, $C_1$–$C_6$-alkoxy-, $C_1$–$C_6$-halogenoalkyl-, $C_1$–$C_6$-halogenoalkoxy-substituted phenyl;

represents optionally halogen-, $C_1$–$C_6$-alkyl-, $C_1$–$C_6$-alkoxy-, $C_1$–$C_6$-halogenoalkyl-, $C_1$–$C_6$-halogenoalkoxy-substituted phenyl-$C_1$–$C_6$-alkyl, represents optionally halogen- and/or $C_1$–$C_6$-alkyl-substituted pyridyl, pyrimidyl, thiazolyl and pyrazolyl, represents optionally halogen- and/or $C_1$–$C_6$-alkyl-substituted phenoxy-$C_1$–$C_6$-alkyl, $R^2$ represents optionally halogen-substituted $C_1$–$C_{20}$-alkyl, $C_2$–$C_{20}$-alkenyl, $C_1$–$C_8$-alkoxy-$C_2$–$C_8$-alkyl, $C_1$–$C_8$-polyalkoxy-$C_2$–$C_8$-alkyl, represents optionally halogen-, nitro-, $C_1$–$C_6$-alkyl-, $C_1$–$C_6$-alkoxy-, $C_1$–$C_6$-halogenoalkyl-substituted phenyl or benzyl, $R^3$, $R^4$ and $R^5$ independently of one another represent optionally halogen-substituted $C_1$–$C_8$-alkyl, $C_1$–$C_8$-alkoxy, $C_1$–$C_8$-alkylamino, di-($C_1$–$C_8$)-alkylamino, $C_1$–$C_8$-alkylthio, $C_2$–$C_5$-alkenylthio, $C_2$–$C_5$-alkenylthio, $C_3$–$C_7$-cycloalkylthio, represent optionally halogen-, nitro-, cyano-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkyl-, $C_1$–$C_4$-halogenoalkyl-substituted phenyl, phenoxy or phenylthio, $R^6$ and $R^7$ independently of one another represent optionally halogen-substituted $C_1$–$C_{20}$-alkyl, $C_1$–$C_{20}$-alkoxy, $C_2$–$C_8$-alkenyl, $C_1$–$C_{20}$-alkoxy-$C_1$–$C_{20}$-alkyl, represent optionally halogen-, $C_1$–$C_{20}$-halogenoalkyl-, $C_1$–$C_{20}$-alkyl- or $C_1$–$C_{20}$-alkoxy-substituted phenyl, represent optionally halogen-, $C_1$–$C_{20}$-alkyl-, $C_1$–$C_{20}$-halogenoalkyl- or $C_1$–$C_{20}$-alkoxy-substituted benzyl or together represent a $C_2$–$C_6$-alkylene ring which is optionally interrupted by oxygen, and at least one agonist and/or antagonist of acetylcholine receptors of the formula (II) are synergistically effective and suitable for controlling animal pests. Owing to this synergism, it is possible to use considerably lower amounts of active compound, i.e. the effect of the mixture is greater than the effect of the individual components. Preference is given to mixtures which comprise the dihydrofuranone derivative of the formula (Ia)

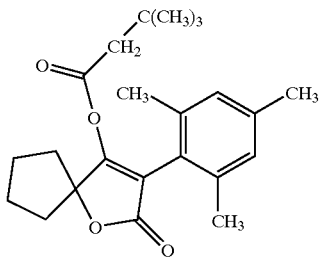

and at least one agonist and/or antagonist of acetylcholine receptors of the formula (II).

The agonists and antagonists of the nicotinic acetylcholine receptors are known compounds, disclosed in the following publications:

European Laid-Open Applications Nos 464 830, 428 941, 425 978, 386 565, 383 091, 375 907, 364 844, 315 826, 259 738, 254 859, 235 725, 212 600, 192 060, 163 855, 154 178, 136 636, 136 686, 303 570, 302 833, 306 696, 189 972, 455 000, 135 956, 471 372, 302 389, 428 941, 376 279, 493 369, 580 553, 649 845, 685 477, 483 055, 580 553;

German Laid-Open Applications Nos 3 639 877, 3 712 307;

Japanese Laid-Open Applications Nos 03 220 176, 02 207 083, 63 307 857, 63 287 764, 03 246 283, 04 9371, 03 279 359, 03 255 072, 05 178 833, 07 173 157, 08 291 171;

U.S. Pat. Nos. 5,034,524, 4,948,798, 4,918,086, 5,039,686, 5,034,404, 5,532,365;

PCT Applications No WO 91/17 659;

French Application No. 2 611 114;

Brazilian Application No. 88 03 621.

The generic formulae and definitions described in these publications, and the individual compounds described therein, are expressly incorporated herein by reference.

Some of these compounds are summarized under the term nitromethylenes, nitroimines and related compounds.

These compounds can preferably be summarized by the formula (II)

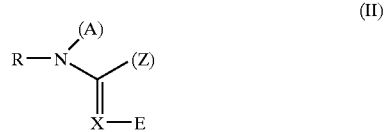

(II)

in which

R represents hydrogen, optionally substituted acyl, alkyl, aryl, aralkyl, heterocyclyl, heteroaryl or heteroarylalkyl radicals;

A represents a monofunctional group from the series consisting of hydrogen, acyl, alkyl, aryl or represents a bifunctional group which is attached to the radical Z;

E represents an electron-withdrawing radical;

X represents the radicals —CH= or =N—, where, instead of an H atom, the radical —CH= can be attached to the radical Z;

Z represents a monofunctional group from the series consisting of alkyl, —O—R, —S—R,

where the radicals R are identical or different and are as defined above, or represents a bifunctional group which is attached to the radical A or the radical X.

Particular preference is given to compounds of the formula (II) in which the radicals are as defined below:

R represents hydrogen and represents optionally substituted radicals from the series consisting of: acyl, alkyl, aryl, aralkyl, heterocyclylalkyl, heteroaryl, heteroarylalkyl.

Acyl radicals which may be mentioned are formyl, alkylcarbonyl, arylcarbonyl, alkylsulphonyl, arylsulphonyl, (alkyl-)-(aryl-)-phosphoryl, which may be substituted for their part.

Alkyls which may be mentioned is $C_1$–$C_{10}$-alkyl, in particular $C_1$–$C_4$-alkyl, specifically methyl, ethyl, i-propyl, sec- or t-butyl, which may be substituted for their part.

Aryls which may be mentioned are phenyl, naphthyl, in particular phenyl.

Aralkyls which may be mentioned are phenylmethyl, phenethyl.

A heterocyclylalkyl which may be mentioned is the radical

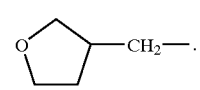

A heteroaryl which may be mentioned is heteroaryl having up to 10 ring atoms and N, O, S, in particular N, as heteroatoms. Specifically, thienyl, furyl, thiazolyl, imidazolyl, pyridyl, benzothiazolyl and pyridazinyl may be mentioned.

Heteroarylalkyls which may be mentioned are heteroarylmethyl, heteroarylethyl having up to 6 ring atoms and N, O, S, in particular N, as heteroatoms, in particular optionally substituted heteroaryl as defined under heteroaryl.

Examples of preferred substituents are:

Alkyl having preferably 1 to 4, in particular 1 or 2, carbon atoms, such as methyl, ethyl, n- and i-propyl and n-, i- and t-butyl; alkoxy having preferably 1 to 4, in particular 1 or 2, carbon atoms, such as methoxy, ethoxy, n- and i-propyloxy and n-, i- and t-butyloxy; alkylthio having preferably 1 to 4, in particular 1 or 2, carbon atoms, such as methylthio, ethylthio, n- and i-propylthio and n-, i- and t-butylthio; halogenoalkyl having preferably 1 to 4, in particular 1 or 2, carbon atoms and preferably 1 to 5, in particular 1 to 3, halogen atoms, where the halogen atoms are identical or different and are preferably fluorine, chlorine or bromine, in particular fluorine, such as trifluoromethyl; hydroxyl; halogen, preferably fluorine, chlorine, bromine and iodine, in particular fluorine, chlorine and bromine; cyano; nitro; amino; monoalkyl- and dialkylamino having preferably 1 to 4, in particular 1 or 2, carbon atoms per alkyl group, such as methylamino, methylethylamino, n- and i-propyl amino and methyl-n-butylamino; carboxyl; carbalkoxy having preferably 2 to 4, in particular 2 or 3, carbon atoms, such as carbomethoxy and carboethoxy; sulpho ($-SO_3H$); alkylsulphonyl having preferably 1 to 4, in particular 1 or 2, carbon atoms, such as methylsulphonyl and ethylsulphonyl; arylsulphonyl having preferably 6 or 10 aryl carbon atoms, such as phenylsulphonyl, and heteroarylamino and heteroarylalkylamino, such as chloropyridylamino and chloropyridylmethylamino.

A represents hydrogen or represents an optionally substituted radical from the series consisting of acyl, alkyl, aryl, which are preferably as defined under R, A furthermore represents a bifunctional group. Mention may be made of optionally substituted alkylene having 1 to 4, in particular 1 to 2, C atoms, where the substituents listed further above may be mentioned as substituents (and where the alkylene groups may be interrupted by heteroatoms from the series consisting of N, O, S).

A and Z together with the atoms to which they are attached may form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups are N-alkyl, where the alkyl of the N-alkyl group preferably contains 1 to 4, in particular 1 or 2, carbon atoms. Methyl, ethyl, n- and i-propyl and n-, i- and t-butyl may be mentioned as alkyl. The heterocyclic ring contains 5 to 7, preferably 5 or 6, ring members.

The following compounds may be mentioned as examples for the compounds of the formula (II) in which A and Z together with the atoms to which they are attached form a ring:

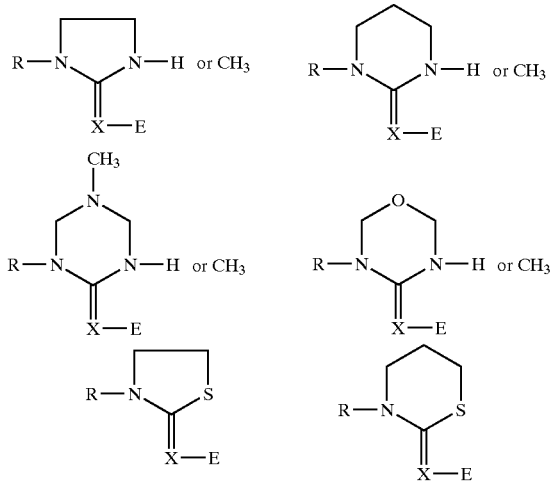

in which
E, R and X have the meanings given above and further below.
E represents an electron-withdrawing radical, and particular mention may be made of $NO_2$, CN, halogenoalkylcarbonyl, such as halogeno-$C_1$–$C_4$alkylcarbonyl, for example $COCF_3$, alkylsulphonyl (for example $SO_2$—$CH_3$), halogenoalkylsulphonyl (for example $SO_2CF_3$) and very particularly $NO_2$ or CN.

X also represents —CH= or —N=. 
Z represents an optionally substituted radical from the series consisting of alkyl, —OR, —SR, —NRR, where R and the substituents preferably have the meanings given above.
Z may, in addition to the abovementioned ring and together with the atom to which it is attached and the radical $$=\overset{|}{C}-$$

instead of X, form a saturated or unsaturated heterocyclic ring. The heterocyclic ring may contain a further 1 or 2 identical or different heteroatoms and/or hetero groups. Preferred heteroatoms are oxygen, sulphur or nitrogen and preferred hetero groups N-alkyl, where the alkyl or the N-alkyl group preferably contains 1 to 4, preferably 1 or 2, carbon atoms. Alkyl which may be mentioned are methyl, ethyl, n- and i-propyl and n-, i- and tbutyl. The heterocyclic ring contains 5 to 7, preferably 5 or 6, ring members.

Examples of the heterocyclic ring which may be mentioned are pyrrolidine, piperidine, piperazine, hexamethyleneimine, morpholine and N-methylpiperazine.

The agonists and antagonists of the nicotinic acetylcholine receptors are particularly preferably compounds of the formula (II) in which
R represents

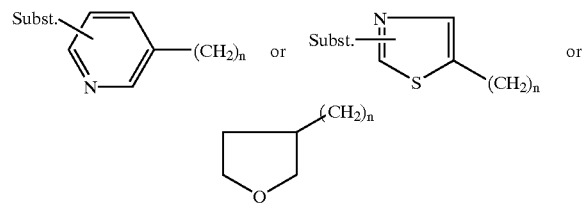

where
n represents 0, 1 or 2, preferably 1,
Subst. represents one of the abovementioned substituents, especially halogen, in particular chlorine, and A, Z, X and E have the meaning given above.
R represents in particular

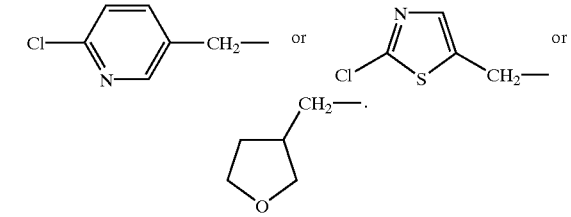

Specifically, the following compounds may be mentioned:

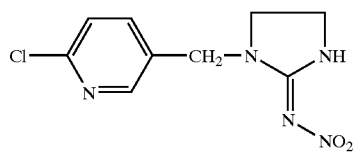

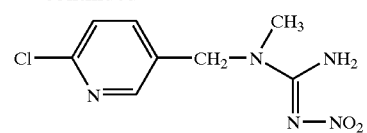
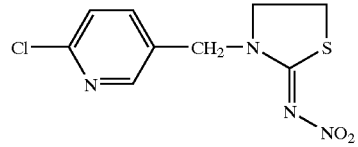
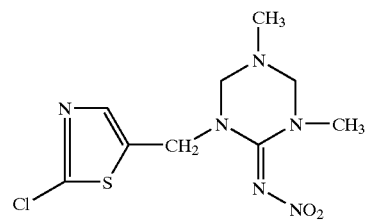
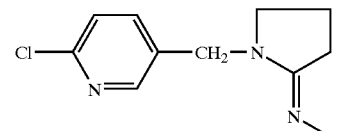
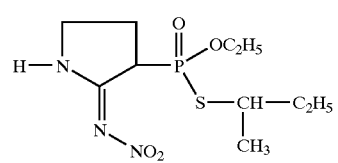
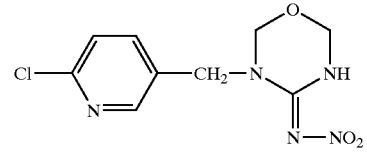
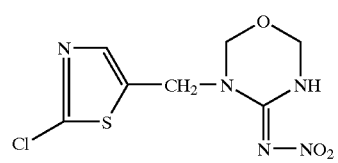
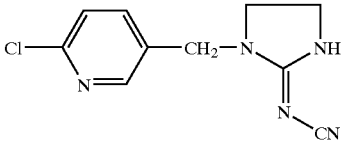
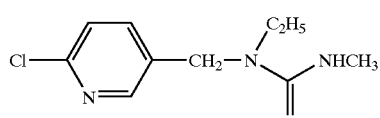
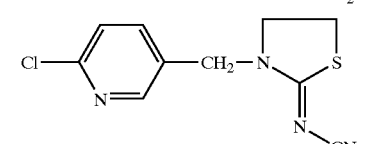
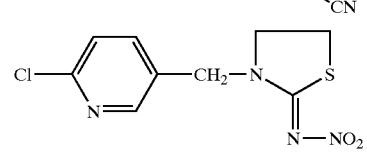
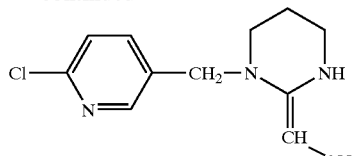
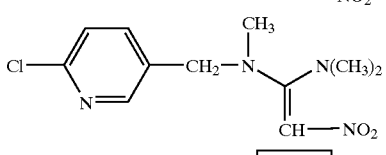
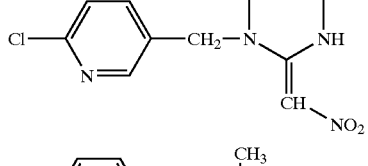
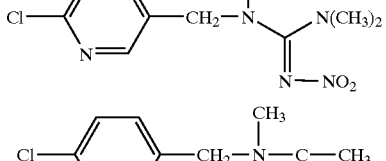
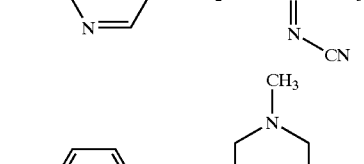
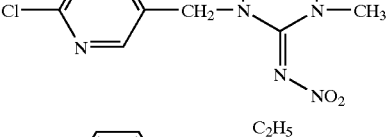
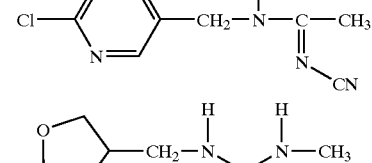
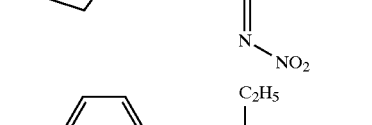
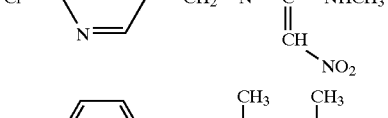
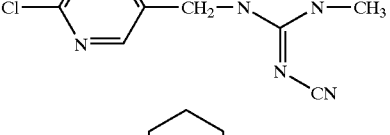
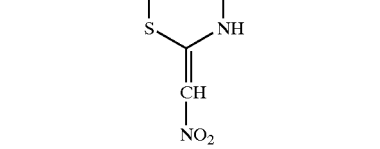

-continued
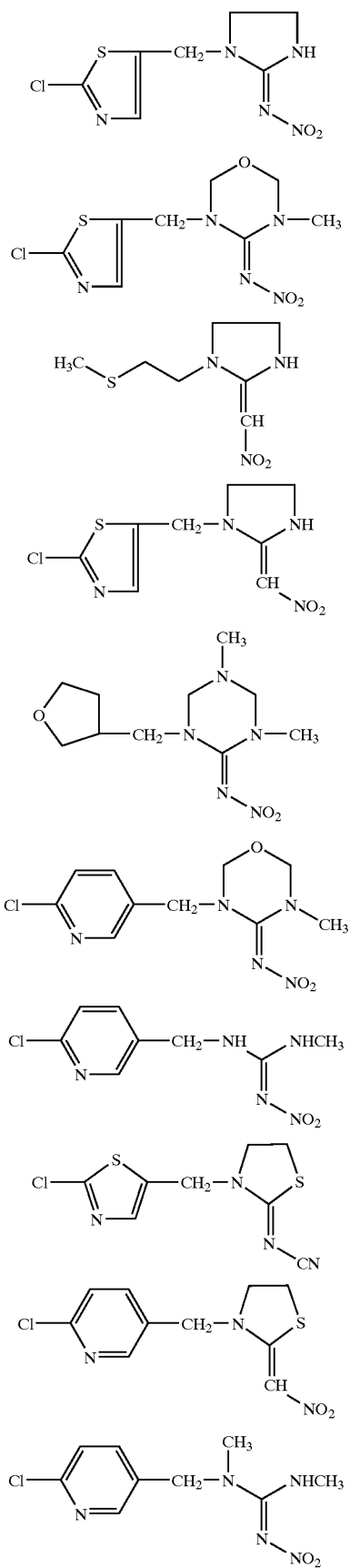
-continued
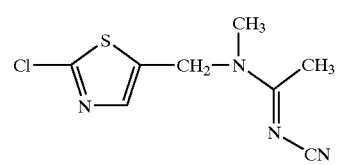
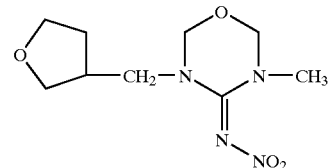
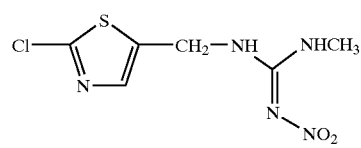
Very particularly preferred agonists and antagonists of the nicotinic acetylcholine receptors are compounds of the following formulae:
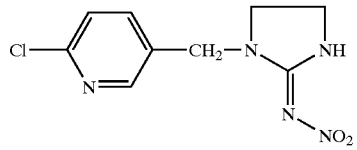
(IIa)
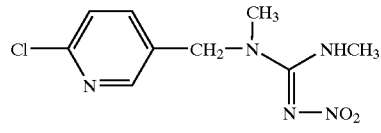
(IIb)
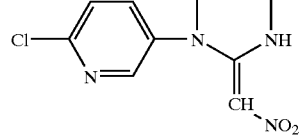
(IIc)
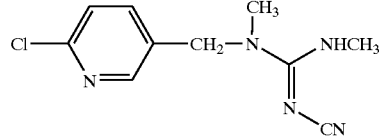
(IId)
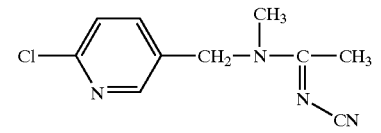
(IIe)
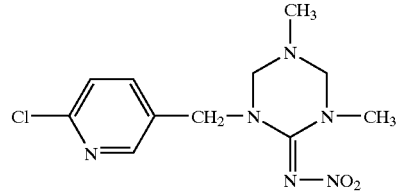
(IIf)

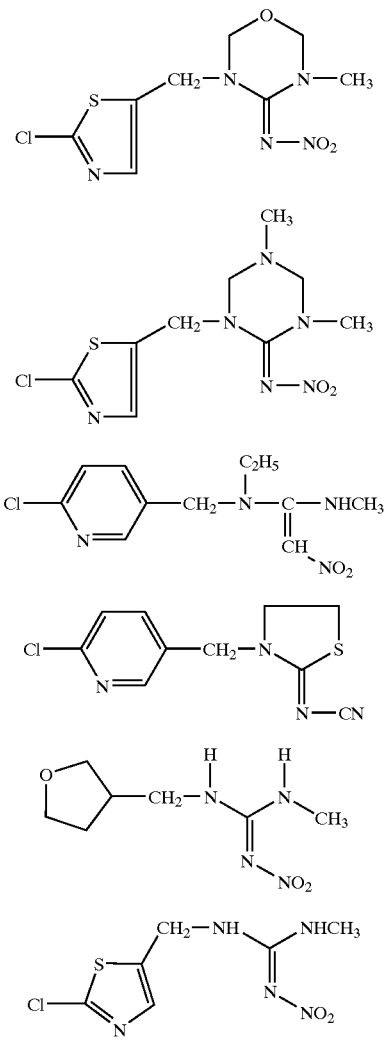

in particular a compound of the following formulae

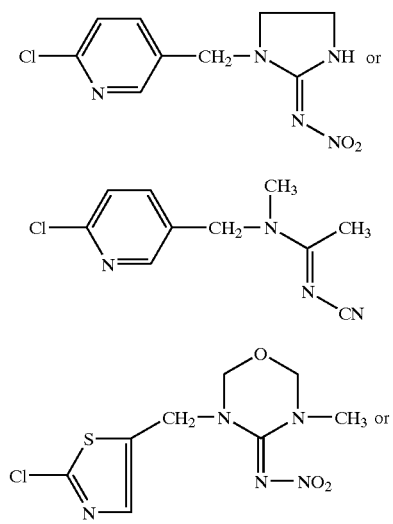

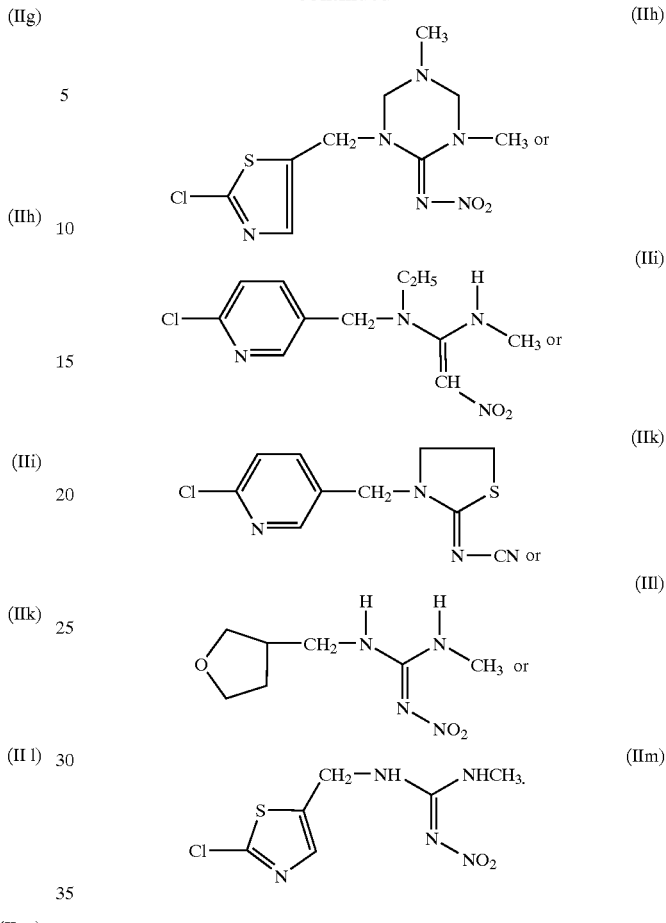

Very particular preference is given to the compounds of the formulae (IIa), (IIk).

Furthermore, very particular preference is given to the compounds of the formulae (IIe), (IIg), (IIh), (IIl), (IIc), (IIm).

The active compound combinations are suitable for controlling animal pests, in particular insects, arachnids and nematodes, which are encountered in agriculture, in forestry, in the protection of stored products and of materials, and in the hygiene sector, and have good plant tolerance and favourable toxicity to warm-blooded animals. They may be preferably employed as crop protection agents. They are active against normally sensitive and resistant species and against all or some stages of development. The abovementioned pests include:

From the order of the Isopoda, for example, *Oniscus asellus*, *Armadillidium vulgare* and *Porcellio scaber*.

From the order of the Diplopoda, for example, *Blaniulus guttulatus*.

From the order of the Chilopoda, for example, *Geophilus carpophagus* and *Scutigera* spp.

From the order of the Symphyla, for example, *Scutigerella immaculata*.

From the order of the Thysanura, for example, *Lepisma saccharina*.

From the order of the Collembola, for example, *Onychiurus armatus*.

From the order of the Orthoptera, for example, *Acheta domesticus*, *Gryllotalpa* spp., *Locusta migratoria migratorioides*, *Melanoplus* spp. and *Schistocerca gregaria*.

From the order of the Blattaria, for example, *Blatta orientalis*, *Periplaneta americana*, *Leucophaea maderae*, *Blattella germanica*.

From the order of the Dermaptera, for example, *Forficula auricularia*.

From the order of the Isoptera, for example, *Reticulitermes* spp.

From the order of the Plithiraptera, for example, *Pediculus humanus corporis, Haematopinus* spp., *Linognathus* spp., *Trichodectes* spp. and *Damalinia* spp.

From the order of the Thysanoptera, for example, *Hercinothrips femoralis, Thrips tabaci, Thrips palmi* and *Frankliniella accidentalis*.

From the order of the Heteroptera, for example, *Eurygaster* spp., *Dysdercus intermedius, Piesma quadrata, Cimex lectularius, Rhodnius prolixus* and *Triatoma* spp.

From the order of the Homoptera, for example, *Aleurodes brassicae, Bemisia tabaci, Trialeurodes vaporariorum, Aphis gossypii, Brevicoryne brassicae, Cryptomyzus ribis, Aphis fabae, Aphis pomi, Eriosoma lanigerum, Hyalopterus arundinis, Phylloxera vastatrix, Pemphigus* spp., *Macrosiphum avenae, Myzus* spp., *Phorodon humuli, Rhopalosiphum padi, Empoasca* spp., *Euscelis bilobatus, Nephotettix cincticeps, Lecanium corni, Saissetia oleae, Laodelphax striatellus, Nilaparvata lugens, Aonidiella aurantii, Aspidiotus hederae, Pseudococcus* spp. and *Psylla* spp.

From the order of the Lepidoptera, for example, *Pectinophora gossypiella, Bupalus piniarius, Cheimatobia brumata, Lithocolletis blancardella, Hyponomeuta padella, Plutella xylostella, Malacosoma neustria, Euproctis chrysorrhoea, Lymantria* spp., *Bucculatrix thurberiella, Phyllocnistis citrella, Agrotis* spp., *Euxoa* spp., *Feltia* spp., *Earias insulana, Heliothis* spp., *Mamestra brassicae, Panolis flammea, Spodoptera* spp., *Trichoplusia ni, Carpocapsa pomonella, Pieris* spp., *Chilo* spp., *Pyrausta nubilalis, Ephestia kuehniella, Galleria mellonella, Tineola bisselliella, Tinea pellionella, Hofmannophila pseudospretella, Cacoecia podana, Capua reticulana, Choristoneura fumiferana, Clysia ambiguella, Homona magnanima, Tortrix viridana, Cnaphalocerus* spp. and *Oulema oryzae*.

From the order of the Coleoptera, for example, *Anobium punctatum, Rhizopertha dorninica, Bruchidius obtectus, Acanthoscelides obtectus, Hylotrupes bajulus, Agelastica alni, Leptinotarsa decemlineata, Phaedon cochleariae, Diabrotica* spp., *Psylliodes chrysocephala, Epilachna varivestis, Atomaria* spp., *Oryzaephilus surinamensis, Anthonomus* spp., *Sitophilus* spp., *Otiorrhynchus sulcatus, Cosmopolites sordidus, Ceuthorrhynchus assimilis, Hypera postica, Dermestes* spp., *Trogoderma* spp., *Anthrenus* spp., *Attagenus* spp., *Lyctus* spp., *Meligethes aeneus, Ptinus* spp., *Niptus hololeucus, Gibbium psylloides, Tribolium* spp., *Tenebrio molitor, Agriotes* spp., *Conoderus* spp., *Melolontha melolontha, Amphimallon soistitialis, Costelytra zealandica* and *Lissorhoptrus oryzophilus*.

From the order of the Hymenoptera, for example, *Diprion* spp., *Hoplocampa* spp., *Lasius* spp., *Monomorium pharaonis* and *Vespa* spp.

From the order of the Diptera, for example, *Aedes* spp., *Anopheles* spp., *Culex* spp., *Drosophila melanogaster, Musca* spp., *Fannia* spp., *Calliphora erythrocephala, Lucilia* spp., *Chrysomyia* spp., *Cuterebra* spp., *Gastrophilus* spp., *Hyppobosca* spp., *Stomoxys* spp., *Oestrus* spp., *Hypoderma* spp., *Tabanus* spp., *Tannia* spp., *Bibio hortulanus, Oscinella frit, Phorbia* spp., *Pegomyia hyoscyami, Ceratitis capitata, Dacus oleae, Tipula paludosa, Hylemyia* spp. and *Liriomyza* spp.

From the order of the Siphonaptera, for example, *Xenopsylla cheopis* and *Ceratophyllus* spp.

From the order of the Arachnida, for example, *Scorpio maurus, Latrodectus mactans, Acarus siro, Argas* spp., *Ornithodoros* spp., *Dermanyssus gallinae, Eriophyes ribis, Phyllocoptruta oleivora, Boophilus* spp., *Rhipicephalus* spp., *Amblyomma* spp., *Hyalomma* spp., *Ixodes* spp., *Psoroptes* spp., *Chorioptes* spp., *Sarcoptes* spp., *Tarsonemus* spp., *Bryobia praetiosa, Panonychus* spp., *Tetranychus* spp., *Hemitarsonemus* spp., and *Brevipalpus* spp.

The phytoparasitic nematodes include, for example, *Pratylenchus* spp., *Radopholus similis, Ditylenchus dipsaci, Tylenchulus semipenetrans, Heterodera* spp., *Globodera* spp., *Meloidogyne* spp., *Aphelenchoides* spp., *Longidorus* spp., *Xiphinema* spp., *Trichodorus* spp. and *Bursaphelenchus* spp.

According to the invention, it is possible to treat all plants and parts of plants. By plants are to be understood here all plants and plant populations such as desired and undesired wild plants or crop plants (including naturally occurring crop plants). Crop plants can be plants which can be obtained by conventional breeding and optimization methods or by biotechnological and genetic engineering methods or combinations of these methods, including the transgenic plants and including plant cultivars which can or cannot be protected by plant breeders certificates. Parts of plants are to be understood as meaning all above-ground and below-ground parts and organs of plants, such as shoot, leaf, flower and root, examples which may be mentioned being leaves, needles, stems, trunks, flowers, shoot-bodies, fruits and seeds and also roots, tubers and rhizomes. Parts of plants also include harvested plants and vegetative and generative propagation material, for example seedlings, tubers, rhizomes, cuttings and seeds.

The treatment of the plants and parts of plants according to the invention with the active compound combinations is carried out directly or by action on their environment, habitat or storage area according to customary treatment methods, for example by dipping, spraying, evaporating, atomizing, broadcasting, brushing-on and in the case of propagation material, in particular in the case of seeds, furthermore by one- or multi-layer coating.

The ratio of the compounds of the formula (I) used and the compounds of the formula (II), and the total amount of the mixture, depends on the type and incidence of the insects. The optimum ratios and total amounts employed can for each application in each case be determined, by test series. In general, the ratio of the compounds of the formula (I) to the compounds of the formula (II) is 1:100 to 100:1, preferably 1:25 to 25:1 and particularly preferably 1:5 to 5:1. These are parts by weight.

The active compound combinations can be converted to the customary formulations, such as solutions, emulsions, wettable powders, suspensions, powders, dusts, pastes, soluble powders, granules, suspension-emulsion concentrates, natural and synthetic materials impregnated with active compound and microencapsulations in polymeric substances.

These formulations are produced in a known manner, for example by mixing the active compounds with extenders, that is, liquid solvents, and/or solid carriers, optionally with the use of surfactants, that is emulsifiers and/or dispersants, and/or foam-formers.

If the extender used is water, it is also possible to employ for example organic solvents as auxiliary solvents. Essentially, suitable liquid solvents are: aromatics such as xylene, toluene or alkylnaphthalenes, chlorinated aromatics or chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol and also their ethers and esters, ketones such as acetone, methyl ethyl ketone, methyl isobutyl ketone or cyclohexanone, strongly polar solvents such as dimethylformamide and dimethyl sulphoxide, and also water.

As solid carriers there are suitable:

for example ammonium salts and ground natural minerals such as kaolins, clays, talc, chalk, quartz, attapulgite, montmorillonite or diatomaceous earth, and ground synthetic minerals, such as highly disperse silica, alumina and silicates; as solid carriers for granules there are suitable: for example crushed and fractionated natural rocks such as calcite, marble, pumice, sepiolite and dolomite, and also synthetic granules of inorganic and organic meals, and granules of organic material such as sawdust, coconut shells, maize cobs and tobacco stalks; as emulsifiers and/or foam-formers there are suitable: for example nonionic and anionic emulsifiers, such as polyoxyethylene fatty acid esters, polyoxyethylene fatty alcohol ethers, for example alkylaryl polyglycol ethers, alkylsulphonates, alkyl sulphates, arylsulphonates and also protein hydrolysates; as dispersants there are suitable: for example lignin-sulphite waste liquors and methylcellulose.

Tackifiers such as carboxymethylcellulose and natural and synthetic polymers in the form of powders, granules or latices, such as gum arabic, polyvinyl alcohol and polyvinyl acetate, as well as natural phospholipids such as cephalins and lecithins, and synthetic phospholipids, can be used in the formulations. Other additives can be mineral and vegetable oils.

It is possible to use colorants such as inorganic pigments, for example iron oxide, titanium oxide and Prussian Blue, and organic dyestuffs, such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95% by weight of active compound, preferably between 0.5 and 90%.

The active compound combinations according to the invention can be present in commercially available formulations and in the use forms, prepared from these formulations, as a mixture with other active compounds, such as insecticides, attractants, sterilizing agents, bactericides, acaricides, nematicides, fungicides, growth-regulating substances or herbicides. The insecticides include, for example, phosphoric acid esters, carbamates, carboxylates, chlorinated hydrocarbons, phenylureas and substances produced by microorganisms, inter alia.

Particularly favourable examples of co-components in mixtures are the following compounds:

Fungicides:

aldimorph, ampropylfos, ampropylfos potassium, andoprim, anilazine, azaconazole, azoxystrobin, benalaxyl, benodanil, benomyl, benzamacril, benzamacryl-isobutyl, bialaphos, binapacryl, biphenyl, bitertanol, blasticidin-S, bromuconazole, bupirimate, buthiobate, calcium polysulphide, capsimycin, captafol, captan, carbendazim, carboxin, carvon, quinomethionate, chlobenthiazone, chlorfenazole, chloroneb, chloropicrin, chlorothalonil, chlozolinate, clozylacon, cufraneb, cymoxanil, cyproconazole, cyprodinil, cyprofuram, debacarb, dichlorophen, diclobutrazole, diclofluanid, diclomezine, dicloran, diethofencarb, difenoconazole, dimethirimol, dimethomorph, diniconazole, diniconazole-M, dinocap, diphenylamine, dipyrithione, ditalimfos, dithianon, dodemorph, dodine, drazoxolon, edifenphos, epoxiconazole, etaconazole, ethirimol, etridiazole, famoxadon, fenapanil, fenarimol, fenbuconazole, fenfuram, fenitropan, fenpiclonil, fenpropidin, fenpropimorph, fentin acetate, fentin hydroxide, ferbam, ferimzone, fluazinam, flumetover, fluoromide, fluquinconazole, flurprimidol, flusilazole, flusulfamide, flutolanil, flutriafol, folpet, fosetyl-aluminium, fosetyl-sodium, fthalide, fuberidazole, furalaxyl, furametpyr, furcarbonil, furconazole, furconazole-cis, furmecyclox, guazatine, hexachlorobenzene, hexaconazole, hymexazole, imazalil, imibenconazole, iminoctadine, iminoctadine albesilate, iminoctadine triacetate, iodocarb, ipconazole, iprobenfos (IBP), iprodione, irumamycin, isoprothiolane, isovaledione, kasugamycin, kresoxim-methyl, copper preparations, such as: copper hydroxide, copper naphthenate, copper oxychloride, copper sulphate, copper oxide, oxine-copper and Bordeaux mixture, mancopper, mancozeb, maneb, meferimzone, mepanipyrim, mepronil, metalaxyl, metconazole, methasulfocarb, methfuroxam, metiram, metomeclam, metsulfovax, mildiomycin, myclobutanil, myclozolin, nickel dimethyldithiocarbamate, nitrothal-isopropyl, nuarimol, ofurace, oxadixyl, oxamocarb, oxolinic acid, oxycarboxim, oxyfenthiin, paclobutrazole, pefurazoate, penconazole, pencycuron, phosdiphen, pimaricin, piperalin, polyoxin, polyoxorim, probenazole, prochloraz, procymidone, propamocarb, propanosine-sodium, propiconazole, propineb, pyrazophos, pyrifenox, pyrimethanil, pyroquilon, pyroxyfur, quinconazole, quintozene (PCNB), sulphur and sulphur preparations, tebuconazole, tecloftalam, tecnazene, tetcyclasis, tetraconazole, thiabendazole, thicyofen, thifluzamide, thiophanate-methyl, thiram, tioxymid, tolclofos-methyl, tolylfluanid, triadimefon, triadimenol, triazbutil, triazoxide, trichlamide, tricyclazole, tridemorph, triflumizole, triforine, triticonazole, uniconazole, validamycin A, vinclozolin, viniconazole, zarilamide, zineb, ziram and also Dagger G,

OK-8705,

OK-8801,

α-(1,1-dimethylethyl)-β-(2-phenoxyethyl)-1H-1,2,4-triazole-1-ethanol,

α-(2,4-dichlorophenyl)-β-fluoro-β-propyl-1H— 1,2,4-triazole-1-ethanol,

α-(2,4-dichlorophenyl)-β-methoxy-α-methyl-1H-1,2,4-triazole-1-ethanol,

α-(5-methyl-1,3-dioxan-5-yl)-β-[[4-(trifluoromethyl)-phenyl]-methylene]-1H-1,2,4-triazole-1-ethanol, (5RS,6RS)-6-hydroxy-2,2,7,7-tetramethyl-5-(1H-1,2,4-triazol-1-yl)-3-octanone, (E)-α-(methoxyimino)-N-methyl-2-phenoxy-phenylacetamide, 1-isopropyl{2-methyl-1-[[[1-(4-methylphenyl)-ethyl]-amino]-carbonyl]-propyl}carbamate, 1-(2,4-dichlorophenyl)-2-(1H-1,2,4-triazol-1-yl)-ethanone-O-(phenylmethyl)-oxime, 1-(2-methyl-1-naphthalenyl)-1H-pyrrole-2,5-dione, 1-(3,5-dichlorophenyl)-3-(2-propenyl)-2,5-pyrrolidindione, 1-[(diiodomethyl)-sulphonyl]-4-methyl-benzene, 1-[[2-(2,4-dichlorophenyl)-1,3-dioxolan-2-yl]-methyl]-1H-imidazole,
1-[[2-(4-chlorophenyl)-3-phenyloxiranyl]-methyl]-1H-1,2,4-triazole,
1-[1-[2-[(2,4-dichlorophenyl)-methoxy]-phenyl]-ethenyl]-1H-imidazole,
1-methyl-5-nonyl-2-(phenylmethyl)-3-pyrrolidinole,
2',6'-dibromo-2-methyl-4'-trifluoromethoxy-4'-trifluoro-methyl-1,3-thiazole-5-carboxanilide,
2,2-dichloro-N-[1-(4-chlorophenyl)-ethyl]-1-ethyl-3-methyl-cyclopropanecarboxamide,
2,6-dichloro-5-(methylthio)-4-pyrimidinyl-thiocyanate, 2,6-dichloro-N-(4-trifluoromethylbenzyl)-benzamide,
2,6-dichloro-N-[[4-(trifluoromethyl)-phenyl]-methyl]-benzamide,
2-(2,3,3-triiodo-2-propenyl)-2H-tetrazole,
2-[(1-methylethyl)-sulphonyl]-5-(trichloromethyl)-1,3,4-thiadiazole,
2-[[6-deoxy-4-O-(4-O-methyl-β-D-glycopyranosyl)-α-D-glucopyranosyl]-amino]-4-methoxy-1H-pyrrolo [2,3-d] pyrimidine-5-carbonitrile,
2-aminobutane,
2-bromo-2-(bromomethyl)-pentanedinitrile,
2-chloro-N-(2,3-dihydro-1,1,3-trimethyl-1H-inden-4-yl)-3-pyridinecarboxamide,
2-chloro-N-(2,6-dimethylphenyl)-N-(isothiocyanatomethyl)-acetamide,
2-phenylphenol (OPP),
3,4-dichloro-1-[4-(difluoromethoxy)-phenyl]-1H-pyrrole-2,5-dione,
3,5-dichloro-N-[cyano[(1-methyl-2-propynyl)-oxy]-methyl]-benzamide,
3-(1,1-dimethylpropyl-1-oxo-1H-indene-2-carbonitrile,
3-[2-(4-chlorophenyl)-5-ethoxy-3-isoxazolidinyl]-pyridine,
4-chloro-2-cyano-N,N-dimethyl-5-(4-methylphenyl)-1H-imidazole-1-sulphonamide, 4-methyl-tetrazolo[1,5-a]quinazolin-5(4H)-one,
8-(1,1-dimethylethyl)-N-ethyl-N-propyl-1,4-dioxaspiro[4.5]decane-2-methanamine,
8-hydroxyquinoline sulphate,
9H-xanthene-2-[(phenylamino)-carbonyl]-9-carboxylic hydrazide,
bis-(1-methylethyl)-3-methyl-4-[(3-methylbenzoyl)-oxy]-2,5-thiophenedicarboxylate,
cis-1-(4-chlorophenyl)-2-(1H-1,2,4-triazol-1-yl)-cycloheptanol,
cis-4-[3-[4-(1,1-dimethylpropyl)-phenyl-2-methylpropyl]-2,6-dimethyl-morpholine hydrochloride,
ethyl [(4-chlorophenyl)-azo]-cyanoacetate,
potassium bicarbonate,
methanetetrathiol-sodium salt,
methyl 1-(2,3-dihydro-2,2-dimethyl-1H-inden-1-yl)-1H-imidazole-5-carboxylate,
methyl N-(2,6-dimethylphenyl)-N-(5-isoxazolylcarbonyl)-DL-alaninate,
methyl N-(chloroacetyl)-N-(2,6-dimethylphenyl)-DL-alaninate,
N-(2,3-dichloro-4-hydroxyphenyl)-1-methyl-cyclohexanecarboxamide,
N-(2,6-dimethylphenyl)-2-methoxy-N-(tetrahydro-2-oxo-3-furanyl)-acetamide, N-(2,6-dimethylphenyl)-2-methoxy-N-(tetrahydro-2-oxo-3-thienyl)-acetamide,
N-(2-chloro-4-nitrophenyl)-4-methyl-3-nitro-benzenesulphonamide,
N-(4-cyclohexylphenyl)-1,4,5,6-tetrahydro-2-pyrimidinamine,
N-(4-hexylphenyl)-1,4,5,6-tetrahydro-2-pyrimidinamine,
N-(5-chloro-2-methylphenyl)-2-methoxy-N-(2-oxo-3-oxazolidinyl)-acetamide,
N-(6-methoxy)-3-pyridinyl)-cyclopropanecarboxamide,
N-[2,2,2-trichloro-1-[(chloroacetyl)-amino]-ethyl]-benzamide,
N-[3-chloro-4,5-bis(2-propinyloxy)-phenyl]-N'-methoxy-methanimidamide,
N-formyl-N-hydroxy-DL-alanine-sodium salt,
O,O-diethyl [2-(dipropylamino)-2-oxoethyl]-ethylphosphoramidothioate,
O-methyl S-phenyl phenylpropylphosphoramidothioate,
S-methyl 1,2,3-benzothiadiazole-7-carbothioate,
spiro[2H]-1-benzopyrane-2,1'(3'H)-isobenzofuran]-3'-one,
Bactericides:
bronopol, dichlorophen, nitrapyrin, nickel dimethyldithiocarbamate, kasugamycin, octhilinone, furancarboxylic acid, oxytetracyclin, probenazole, streptomycin, tecloftalam, copper sulphate and other copper preparations.

Insecticides/Acaricides/Nematicides:
abamectin, acephate, acetamiprid, acrinathrin, alanycarb, aldicarb, aldoxycarb, alphacypermethrin, alphamethrin, amitraz, avermectin, AZ 60541, azadirachtin, azamethiphos, azinphos A, azinphos M, azocyclotin,

*Bacillus popilliae, Bacillus sphaericus, Bacillus subtilis, Bacillus thuringiensis*, baculoviruses, *Beauveria bassiana, Beauveria tenella*, bendiocarb, benfuracarb, bensultap, benzoximate, betacyfluthrin, bifenazate, bifenthrin, bioethanomethrin, biopermethrin, BPMC, bromophos A, bufencarb, buprofezin, butathiofos, butocarboxim, butylpyridaben, cadusafos, carbaryl, carbofuran, carbophenothion, carbosulfan, cartap, chloethocarb, chlorethoxyfos, chlorfenapyr, chlorfenvinphos, chlorfluazuron, chlormephos, chlorpyrifos, chlorpyrifos M, chlovaporthrin, cis-resmethrin, cispermethrin, clocythrin, cloethocarb, clofentezine, cyanophos, cycloprene, cycloprothrin, cyfluthrin, cyhalothrin, cyhexatin, cypermethrin, cyromazine, deltamethrin, demeton M, demeton S, demeton-S-methyl, diafenthiuron, diazinon, dichlorvos, diflubenzuron, dimethoate, dimethylvinphos, diofenolan, disulfoton, docusat-sodium, dofenapyn, eflusilanate, emamectin, empenthrin, endosulfan, *Entomopfthora* spp., esfenvalerate, ethiofencarb, ethion, ethoprophos, etofenprox, etoxazole, etrimfos, fenamiphos, fenazaquin, fenbutatin oxide, fenitrothion, fenothiocarb, fenoxacrim, fenoxycarb, fenpropathrin, fenpyrad, fenpyrithrin, fenpyroximate, fenvalerate, fipronil, fluazinam, fluazuron, flubrocythrinate, flucycloxuron, flucythrinate, flufenoxuron, flutenzine, fluvalinate, fonophos, fosmethilan, fosthiazate, fubfenprox, furathiocarb, granulosis viruses,
halofenozide, HCH, heptenophos, hexaflumuron, hexythiazox, hydroprene,
imidacloprid, isazofos, isofenphos, isoxathion, ivermectin,
nuclear polyhedrosis viruses,
lambda-cyhalothrin, lufenuron,
malathion, mecarbam, metaldehyde, methamidophos, *Metharhizium anisopliae, Metharhizium flavoviride*, methidathion, methiocarb, methomyl, methoxyfenozide, metolcarb, metoxadiazone, mevinphos, milbemectin, monocrotophos,
naled, nitenpyram, nithiazine, novaluron,
omethoate, oxamyl, oxydemethon M,
*Paecilomyces fumosoroseus*, parathion A, parathion M, permethrin, phenthoate, phorate, phosalone, phosmet, phosphamidon, phoxim, pirimicarb, pirimiphos A, pirimiphos M, profenofos, promecarb, propoxur, prothiofos, prothoate, pymetrozine, pyraclofos, pyresmethrin, pyrethrum, pyridaben, pyridathion, pyrimidifen, pyriproxyfen, quinalphos, ribavirin, salithion, sebufos, silafluofen, spinosad, sulfotep, sulprofos, tau-fluvalinate, tebufenozide, tebufenpyrad, tebupirimiphos, teflubenzuron, tefluthrin, temephos, temivinphos, terbufos, tetrachlorvinphos, theta-cypermethrin, thiamethoxam, thiapronil, thiatriphos, thiocyclam hydrogen oxalate, thiodicarb, thiofanox, thuringiensin, tralocythrin, tralomethrin, triarathene, triazamate, triazophos, triazuron, trichlophenidine, trichlorfon, triflumuron, trimethacarb, vamidothion, vaniliprole, *Verticillium lecanii,*

YI 5302, zeta-cypermethrin, zolaprofos, (1R-cis)-[5-(phenylmethyl)-3-furanyl]-methyl-3-[(dihydro-2-oxo-3 (2H)-furanylidene)-methyl]-2,2-dimethylcyclopropanecarboxylate, (3-phenoxyphenyl)-methyl-2,2,3,3-tetramethylcyclopropanecarboxylate, 1[(2-chloro-5-thiazolyl)methyl]tetrahydro-3,5-dimethyl-N-nitro-1,3,5-triazine-2(1H)-imine, 2-(2-chloro-6-fluorophenyl)-4-[4-(1,1-dimethylethyl) phenyl]-4,5-dihydro-oxazole, 2-(acetyloxy)-3-dodecyl-1,4-naphthalenedione, 2-chloro-N-[[[4-(1-phenylethoxy)-phenyl]-amino]-carbonyl]-benzamide, 2-chloro-N-[[[4-(2,2-dichloro-1,1-difluoroethoxy)-phenyl]-amino]-carbonyl]benzamide, 3-methylphenyl propylcarbamate, 4-[4-(4-ethoxyphenyl)-4-methylpentyl]-1-fluoro-2-phenoxy-benzene, 4-chloro-2-(1,1-dimethylethyl)-5-[[2-(2,6-dimethyl-4-phenoxyphenoxy)ethyl]thio]-3(2H)-pyridazinone, 4-chloro-2-(2-chloro-2-methylpropyl)-5-[(6-iodo-3-pyridinyl)methoxy]-3(2H)-pyridazinone, 4-chloro-5-[(6-chloro-3-pyridinyl)methoxy]-2-(3,4-dichlorophenyl)-3(2H)-pyridazinone,

*Bacillus thuringiensis* strain EG-2348,

[2-benzoyl-1-(1,1-dimethylethyl)-hydrazinobenzoic acid, 2,2-dimethyl-3-(2,4-dichlorophenyl)-2-oxo-1-oxaspiro[4.5]dec-3-en-4-yl butanoate,

[3-[(6-chloro-3-pyridinyl)methyl]-2-thiazolidinylidene]-cyanamide, dihydro-2-(nitromethylene)-2H-1,3-thiazine-3(4H)-carboxaldehyde, ethyl [2-[[1,6-dihydro-6-oxo-1-(phenylmethyl)-4-pyridazinyl]oxy]ethyl]-carbamate, N-(3,4,4-trifluoro-1-oxo-3-butenyl)-glycine, N-(4-chlorophenyl)-3-[4-(difluoromethoxy)phenyl]-4,5-dihydro-4-phenyl-1H-pyrazole-1-carboxamide, N-[(2-chloro-5-thiazolyl)methyl]-N'-methyl-N"-nitro-guanidine, N-methyl-N'-(1-methyl-2-propenyl)-1,2-hydrazinedicarbothioamide, N-methyl-N'-2-propenyl-1,2-hydrazinedicarbothioamide, O,O-diethyl [2-(dipropylamino)-2-oxoethyl]-ethylphosphoramidothioate.

It is also possible to admix other known active compounds, such as herbicides or fertilizers and growth regulators.

When used as insecticides, the active compound combinations according to the invention can furthermore be present in their commercially available formulations and in the use forms, prepared from these formulations, as a mixture with synergistic agents. Synergistic agents are compounds which increase the action of the active compounds, without it being necessary for the synergistic agent added to be active itself.

The active compound content of the use forms prepared from the commercially available formulations can vary within wide limits. The active compound concentration of the use forms can be from 0.0000001 to 95% by weight of active compound, preferably between 0.0001 and 1% by weight.

The compounds are employed in a customary manner appropriate for the use forms.

When used against hygiene pests and pests of stored products, the active compound combinations are distinguished by an excellent residual action on wood and clay as well as a good stability to alkali on limed substrates.

The active compound combinationss according to the invention act not only against plant, hygiene and stored product pests, but also in the veterinary medicine sector against animal parasites (ectoparasites), such as hard ticks, soft ticks, mange mites, leaf mites, flies (biting and licking), parasitic fly larvae, lice, hair lice, feather lice and fleas. These parasites include:

From the order of the Anoplurida, for example, *Haematopinus* spp., *Linognathus* spp., *Pediculus* spp., *Phtirus* spp. and *Solenopotes* spp.

From the order of the Mallophagida and the suborders Amblycerina and Isclnocerina, for example, *Trimenopon* spp., *Menopon* spp., *Trinoton* spp., *Bovicola* spp., *Werneckiella* spp., *Lepikentron* spp., *Damalina* spp., *Trichodectes* spp. and *Felicola* spp.

From the order of the Diptera and the suborders Nematocerina and Brachycerina, for example. *Aedes* spp., *Anopheles* spp., *Culex* spp., *Simulium* spp., *Eusimulium* spp., *Phlebotomus* spp., *Lutzomyia* spp., *Culicoides* spp., *Chrysops* spp., Hybomitra spp., *Atylotus* spp., *Tabanus* spp., *Haematopota* spp., *Philipomyia* spp., *Braula* spp., *Musca* spp., *Hydrotaea* spp., *Stomoxys* spp., *Haematobia* spp., *Morellia* spp., *Fannia* spp., *Glossina* spp., *Calliphora* spp., *Lucilia* spp., *Chrysomyia* spp., *Wohlfahrtia* spp., *Sarcophaga* spp., *Oestrus* spp., *Hypoderma* spp., *Gasterophilus* spp., *Hippobosca* spp., *Lipoptena* spp. and *Melophagus* spp.

From the order of the Siphonapterida, for example *Pulex* spp., *Ctenocephalides* spp., *Xenopsylla* spp. and *Ceratophyllus* spp.

From the order of the Heteropterida, for example, *Cimex* spp., *Triatoma* spp., *Rhodnius* spp. and *Panstrongylus* spp.

From the order of the Blattarida, for example *Blatta orientalis, Periplaneta americana, Blattela germanica* and *Supella* spp.

From the subclass of the Acaria (Acarida) and the orders of the Meta- and Mesostigmata, for example, *Argas* spp., *Omithodorus* spp., *Otobius* spp., *Ixodes* spp., *Amblyomma* spp., *Boophilus* spp., *Dermacentor* spp., *Haemophysalis* spp., *Hyalomma* spp., *Rhipicephalus* spp., *Dermanyssus* spp., *Raillietia* spp., *Pneumonyssus* spp., *Stemostoma* spp. and *Varroa* spp.

From the order of the Actinedida (Prostigmata) und Acaridida (Astigmata), for example, *Acarapis* spp., *Cheyletiella* spp., *Ornithocheyletia* spp., *Myobia* spp., *Psorergates* spp., *Demodex* spp., *Trombicula* spp., *Listrophorus* spp., *Acarus* spp., *Tyrophagus* spp., *Caloglyphus* spp., *Hypodectes* spp., *Pterolichus* spp., *Psoroptes* spp., *Chorioptes* spp., *Otodectes* spp., *Sarcoptes* spp., *Notoedres* spp., *Knemidocoptes* spp., *Cytodites* spp. and *Laminosioptes* spp.

The active compound combinations according to the invention are also suitable for controlling arthropods which infest agricultural productive livestock, such as, for example, cattle, sheep, goats, horses, pigs, donkeys, camels, buffalo, rabbits, chickens, turkeys, ducks, geese and bees, other pets, such as, for example, dogs, cats, caged birds and aquarium fish, and also so-called test animals, such as, for example, hamsters, guinea pigs, rats and mice. By controlling these arthropods, cases of death and reduction in productivity (for meat, milk, wool, hides, eggs, honey etc.) should be diminished, so that more economic and easier animal husbandry is possible by use of the active compounds according to the invention.

The active compound combinations according to the invention are used in the veterinary sector in a known manner by enteral administration in the form of, for example, tablets, capsules, potions, drenches, granules, pastes, boluses, the feed-through process and suppositories, by parenteral administration, such as, for example, by injection (intramuscular, subcutaneous, intravenous, intraperitoneal and the like), implants by nasal administration, by dermal use in the form, for example, of dipping or bathing, spraying, pouring on and spotting on, washing and powdering, and also with the aid of moulded articles containing the active compound, such as collars, ear marks, tail marks, limb bands, halters, marking devices and the like.

When used for cattle, poultry, pets and the like, the active compounds can be used as formulations (for example powders, emulsions, free-flowing compositions), which comprise the active compounds in an amount of 1 to 80% by weight, directly or after 100 to 10 000-fold dilution, or they can be used as a chemical bath.

It has furthermore been found that the active compound combinations according to the invention also have a strong insecticidal action against insects which destroy industrial materials.

The following insects may be mentioned as examples and as preferred—but without a limitation:

Beetles, such as
*Hylotrupes bajulus, Chlorophorus pilosis, Anobium punctatum, Xestobium rufovillosum, Ptilinus pecticornis, Dendrobium pertinex, Ernobius mollis, Priobium carpini, Lyctus brunneus, Lyctus africanus, Lyctus planicollis, Lyctus linearis, Lyctus pubescens, Trogoxylon aequale, Minthes rugicollis, Xyleborus* spec. *Tryptodendron* spec. *Apate monachus, Bostrychus capucins, Heterobostrychus brunneus, Sinoxylon* spec. *Dinoderus minutus.*

Hymenopterons, such as
*Sirex juvencus, Urocerus gigas, Urocerus gigas taignus, Urocerus augur.*

Termites, such as
*Kalotermes flavicollis, Cryptotermes brevis, Heterotermes indicola, Reticulitermes flavipes, Reticulitermes santonensis, Reticulitermes lucifugus, Mastotermes darwiniensis, Zootermopsis nevadensis, Coptotermes formosanus.*

Bristletails, such as *Lepisma saccarina.*

Industrial materials in the present connection are to be understood as meaning nonliving materials, such as, preferably, plastics, adhesives, sizes, papers and cards, leather, wood and processed wood products and coating compositions.

Wood and processed wood products are materials to be protected, especially preferably, from insect infestation.

Wood and processed wood products which can be protected by the agent according to the invention or mixtures comprising this are to be understood as meaning, for example: building timber, wooden beams, railway sleepers, bridge components, boat jetties, wooden vehicles, boxes, pallets, containers, telegraph poles, wood panelling, wooden windows and doors, plywood, chipboard, joinery or wooden products which are used quite generally in house-building or in building joinery.

The active compound combinations can be used as such, in the form of concentrates or in generally customary formulations, such as powders, granules, solutions, suspensions, emulsions or pastes.

The formulations mentioned can be prepared in a manner known per se, for example by mixing the active compounds with at least one solvent or diluent, emulsifier, dispersing agent and/or binder or fixing agent, a water repellent, if appropriate siccatives and UV stabilizers and if appropriate dyestuffs and pigments, and also other processing auxiliaries.

The insecticidal compositions or concentrates used for the preservation of wood and wood-derived timber products comprise the active compound according to the invention in a concentration of 0.0001 to 95% by weight, in particular 0.001 to 60% by weight.

The amount of the compositions or concentrates employed depends on the nature and occurrence of the insects and on the medium. The optimum amount employed can be determined for the use in each case by a series of tests. In general, however, it is sufficient to employ 0.0001 to 20% by weight, preferably 0.001 to 10% by weight, of the active compound, based on the material to be preserved.

Solvents and/or diluents which are used are an organic chemical solvent or solvent mixture and/or an oily or oil-like organic chemical solvent or solvent mixture of low volatility and/or a polar organic chemical solvent or solvent mixture and/or water, and if appropriate an emulsifier and/or wetting agent.

Organic chemical solvents which are preferably used are oily or oil-like solvents having an evaporation number above 35 and a flashpoint above 30° C., preferably above 45° C. Substances which are used as such oily or oil-like water-insoluble solvents of low volatility are appropriate mineral oils or aromatic fractions thereof, or solvent mixtures containing mineral oils, preferably white spirit, petroleum and/or alkylbenzene.

Mineral oils having a boiling range from 170 to 220° C., white spirit having a boiling range from 170 to 220° C., spindle oil having a boiling range from 250 to 350° C., petroleum and aromatics having a boiling range from 160 to 280° C., terpentine oil and the like, are advantageously employed.

In a preferred embodiment, liquid aliphatic hydrocarbons having a boiling range from 180 to 210° C. or high-boiling mixtures of aromatic and aliphatic hydrocarbons having a boiling range from 180 to 220° C. and/or spindle oil and/or monochloronaphthalene, preferably α-monochloronaphthalene, are used.

The organic oily or oil-like solvents of low volatility which have an evaporation number above 35 and a flashpoint above 30° C., preferably above 45° C., can be replaced in part by organic chemical solvents of high or medium volatility, providing that the solvent mixture likewise has an evaporation number above 35 and a flashpoint above 30° C., preferably above 45° C., and that the insecticide/fungicide mixture is soluble or emulsifiable in this solvent mixture.

According to a preferred embodiment, some of the organic chemical solvent or solvent mixture is replaced by an aliphatic polar organic chemical solvent or solvent mixture. Aliphatic organic chemical solvents containing hydroxyl and/or ester and/or ether groups, such as, for example, glycol ethers, esters or the like, are preferably used.

Organic chemical binders which are used in the context of the present invention are the synthetic resins and/or binding drying oils which are known per se, are water-dilutable and/or are soluble or dispersible or emulsifiable in the organic chemical solvents employed, in particular binders consisting of or comprising an acrylate resin, a vinyl resin, for example polyvinyl acetate, polyester resin, polycondensation or polyaddition resin, polyurethane resin, alkyd resin or modified alkyd resin, phenolic resin, hydrocarbon resin, such as indene-cumarone resin, silicone resin, drying vegetable oils and/or drying oils and/or physically drying binders based on a natural and/or synthetic resin.

The synthetic resin used as the binder can be employed in the form of an emulsion, dispersion or solution. Bitumen or bituminous substances can also be used as binders in an amount of up to 10% by weight. Dyestuffs, pigments, water-repelling agents, odour correctants and inhibitors or anticorrosive agents and the like which are known per se can additionally be employed.

It is preferred according to the invention for the composition or concentrate to comprise, as the organic chemical binder, at least one alkyd resin or modified alkyd resin and/or one drying vegetable oil. Alkyd resins having an oil content of more than 45% by weight, preferably 50 to 68% by weight, are preferably used according to the invention.

All or some of the binder mentioned can be replaced by a fixing agent (mixture) or a plasticizer (mixture). These additives are intended to prevent evaporation of the active compounds and crystallization or precipitation. They preferably replace 0.01 to 30% of the binder (based on 100% of the binder employed).

The plasticizers originate from the chemical classes of phthalic acid esters, such as dibutyl, dioctyl or benzyl butyl phthalate, phosphoric acid esters, such as tributyl phosphate, adipic acid esters, such as di-(2-ethylhexyl) adipate, stearates, such as butyl stearate or amyl stearate, oleates, such as butyl oleate, glycerol ethers or higher molecular weight glycol ethers, glycerol esters and p-toluenesulphonic acid esters.

Fixing agents are based chemically on polyvinyl alkyl ethers, such as, for example, polyvinyl methyl ether or ketones, such as benzophenone or ethylenebenzophenone.

Possible solvents or diluents are, in particular, also water, if appropriate as a mixture with one or more of the above-mentioned organic chemical solvents or diluents, emulsifiers and dispersing agents.

Particularly effective preservation of wood is achieved by impregnation processes on a large industrial scale, for example vacuum, double vacuum or pressure processes.

The ready-to-use compositions can also comprise other insecticides, if appropriate, and also one or more fungicides, if appropriate.

The active compound combinations according to the invention can also be used for protecting against colonization of articles, especially ships hulls, screens, nets, constructions, quays and signalling equipment, which come into contact with seawater or brackish water.

Colonization by sessile Oligochaetae, such as Serpulidae, and by shellfish and species of the group Ledamorpha (goose barnacles), such as various *Lepas* and *Scalpellum* species, or by species of the group Balanomorpha (acorn barnacles), such as *Balanus* or *Pollicipes* species, increases the frictional resistance of ships and leads as a result, through increased energy consumption and frequent spells in dry dock, to a marked increase in the operating costs.

In addition to colonization by algae, for example *Ectocarpus* sp. and *Ceramium* sp., particular importance is attached to infestation by sessile Entomostraca groups, which are comprised under the name Cirripedia (cirriped crustacea).

Surprisingly, it has now been found that the active compound combinations according to the invention have a good antifouling (anti-colonization) effect.

By using active compound combinations according to the invention it is possible to dispense with the use of heavy metals, such as, for example, in bis(trialkyltin) sulphides, tri-n-butyltin laurate, tri-n-butyltin chloride, copper(I) oxide, triethyltin chloride, tri-n-butyl(2-phenyl-4-chlorophenoxy)-tin, tributyltin oxide, molybdenum-disulphide, antimony oxide, polymeric butyl titanate, phenyl-(bispyridine)-bismuth-chloride, tri-n-butyltin fluoride, manganese ethylenebisthiocarbamate, zinc dimethyl-dithiocarbamate, zinc ethylenebisthiocarbamate, the zinc and copper salts of 2-pyridinethiol 1-oxide, bisdimethyldithiocarbamoylzinc ethylenebisthiocarbamate, zinc oxide, copper(I) ethylene-bisdithiocarbamate, copper thiocyanate, copper-naphthenate and tributyltin halides, or substantially to reduce the concentration of these compounds.

If appropriate, the ready-to-use antifouling paints may comprise yet further active compounds, preferably algicides, fungicides, herbicides, molluscicides or other active antifouling active compounds.

Preferred co-components for the antifouling compositions according to the invention are:

algicides such as
2-tert-butylamino-4-cyclopropylamino-6-methylthio-1,3,5-triazine, dichlorophen, diuron, endothal, fentin acetate, isoproturon, methabenzthiazuron, oxyfluorfen, quinoclamine and terbutryn;

fungicides such as
cyclohexyl-benzo[b]thiophenecarboxamide S,S-dioxide, dichlofluanid, fluor-folpet, 3-iodo-2-propinyl butylcarbamate, tolylfluanid and azoles such as
azaconazole, cyproconazole, epoxyconazole, hexaconazole, metconazole, propiconazole and tebuconazole;

molluscicides such as
fentin acetate, metaldehyde, methiocarb, niclosamid, thiodicarb and trimethacarb;

or customary active antifouling compounds such as
4,5-dichloro-2-octyl-4-isothiazolin-3-one, diiodomethyl paratryl sulfone, 2-(N,N-dimethylthiocarbamoylthio)-5-nitrothiazyl, potassium, copper, sodium and zinc salts of 2-pyridinethiole 1-oxide, pyridine triphenylborane, tetrabutyldistannoxane, 2,3,-5,6-tetrachloro-4-(methylsulphonyl)-pyridine, 2,4,5,6-tetrachloroisophthalonitrile, tetramethylthiuram disulphide and 2,4,6-trichlorophenyl-maleimide.

The antifouling compositions used comprise the active compound in a concentration of from 0.001 to 50% by weight, in particular from 0.01 to 20% by weight.

The antifouling compositions according furthermore comprise the customary components as described, for example, in Ungerer, *Chem. Ind.* 1985, 37, 730–732 and Williams, Antifouling Marine Coatings, Noyes, Park Ridge, 1973.

In addition to the algicidal, fungicidal, molluscicidal and insecticidal active compounds, antifouling coating compositions comprise, in particular, binders.

Examples of acknowledged binders are polyvinyl chloride in a solvent system, chlorinated rubber in a solvent system; acrylic resins in a solvent system especially in an aqueous system, vinyl chloride/vinyl acetate copolymer systems in the form of aqueous dispersions or in the form of organic solvent systems, butadiene/styrene/acrylonitrile rubbers, drying oils, such as linseed oil, resin esters or modified hard resins in combination with tar or bitumen, asphalt and also epoxy compounds, small amounts of chlorinated rubber, chlorinated polypropylene and vinyl resins.

The coating compositions also optionally include inorganic pigments, organic pigments or dyestuffs, which are preferably insoluble in salt water. The coating compositions may also comprise materials such as rosin, for a controlled release of the active compounds. The coats may also include plasticizers, modifying agents which influence the rheological properties, and other conventional constituents. The active compound combinations according to the invention can also be incorporated into self-polishing antifouling systems.

The active compounds are also suitable for controlling animal pests, in particular insects, arachnids and mites, which are encountered in closed rooms, such as, for example, flats, factory halls, offices, vehicle cabins and the like. They can be used on their own or in combination with other active compounds and auxiliaries in household insecticidal products for controlling these pests. They are active against sensitive and resistant species and against all development stages. These pests include:

From the order of the Scorpionidea, for example, *Buthus occitanus*.

From the order of the Acarina, for example, *Argas persicus, Argas reflexus, Bryobia* ssp., *Dermanyssus gallinae, Glyciphagus domesticus, Ornithodorus moubat, Rhipicephalus sanguineus, Trombicula alfreddugesi, Neutrombicula autumnalis, Dermatophagoides pteronissimus, Dermatophagoides forinae*.

From the order of the Araneae, for example, *Aviculariidae, Araneidae*.

From the order of the Opiliones, for example, *Pseudoscorpiones chelifer, Pseudoscorpiones cheiridium, Opiliones phalangium*.

From the order of the Isopoda, for example, *Oniscus asellus, Porcellio scaber*.

From the order of the Diplopoda, for example, *Blaniulus guttulatus, Polydesmus* spp.

From the order of the Chilopoda, for example, *Geophilus* spp.

From the order of the Zygentoma, for example, *Ctenolepisma* spp., *Lepisma saccharina, Lepismodes inquilinus*.

From the order of the Blattaria, for example, *Blatta orientalies, Blattella germanica, Blattella asahinai, Leucophaea maderae, Panchlora* spp., *Parcoblatta* spp., *Periplaneta australasiae, Periplaneta americana, Periplaneta brunnea, Periplaneta fuliginosa, Supella longipalpa*.

From the order of the Saltatoria, for example, *Acheta domesticus*.

From the order of the Dermaptera, for example, *Forficula auricularia*.

From the order of the Isoptera, for example, *Kalotermes* spp., *Reticulitermes* spp.

From the order of the Psocoptera, for example, *Lepinatus* spp., *Liposcelis* spp.

From the order of the Coleptera, for example, *Anthrenus* spp., *Attagenus* spp., *Dermestes* spp., *Latheticus oryzae, Necrobia* spp., *Ptinus* spp., *Rhizopertha dominica, Sitophilus granarius, Sitophilus oryzae, Sitophilus zeamais, Stegobium paniceum*.

From the order of the Diptera, for example, *Aedes aegypti, Aedes albopictus, Aedes taeniorhynchus, Anopheles* spp., *Calliphora erythrocephala, Chrysozona pluvialis, Culex quinquefasciatus, Culex pipiens, Culex tarsalis, Drosophila* spp., *Fannia canicularis, Musca domestica, Phlebotomus* spp., *Sarcophaga camaria, Simulium* spp., *Stomoxys calcitrans, Tipula paludosa*.

From the order of the Lepidoptera, for example, *Achroia grisella, Galleria mellonella, Plodia interpunctella, Tinea cloacella, Tinea pellionella, Tineola bisselliella*.

From the order of the Siphonaptera, for example, *Ctenocephalides canis, Cteiiocephalides felis, Pulex irritans, Tunga penetrans, Xenopsylla cheopis*.

From the order of the Hymenoptera, for example, *Camponotus herculeanus, Lasius fuliginosus, Lasius niger, Lasius umbratus, Monomorium pharaonis, Paravespula* spp., *Tetramorium caespitum*.

From the order of the Anoplura, for example, *Pediculus humanus capitis, Pediculus humanus corporis, Phthirus pubis*.

From the order of the Heteroptera, for example, *Cimex hemipterus, Cimex lectularius, Rhodinus prolixus, Triatoma infestans*.

In the field of the household insecticides, they are used on their own or in combination with other suitable active compounds, such as phosphoric acid esters, carbamates, pyrethroids, growth regulators or active compounds from other known classes of insecticides.

Application is carried out in the form of aerosols, unpressurized sprays, for example pump and atomizer sprays, nebulizers, foggers, foams, gels, vaporizer products with vaporizer tablets made of cellulose or plastic, liquid vaporizers, gel and membrane vaporizers, propeller-operated vaporizers, energyless or passive vaporizer systems, moth papers, moth sachets and moth gels, as granules or dusts, in baits for scattering or bait stations.

When using the active compound combinations according to the invention, the application rates can be varied within a relatively wide range, depending on the kind of application. In the treatment of parts of plants, the application rates of the active compound combination are generally between 0.1 and 10 000 g/ha, preferably between 10 and 1 000 g/ha.

The good insecticidal and acaricidal activity of the active compound combinations according to the invention is evident from the examples below. While the individual active compounds exhibit weaknesses with regard to activity, the combinations have an activity which exceeds a simple addition of activities.

A synergistic effect of insecticides and acaricides is always present when the activity of the active compound combinations exceeds the total of the activities of the active compounds when applied individually.

The expected activity for a given combinatin of two active compounds can be calculated as follows (according to S. R. Colby, Weeds 15 (1967), 20–22):

If
$X$ is the efficacy when applying the active compound A at an application rate of m g/ha or at a concentration of m ppm,
$Y$ is the efficacy when applying the active compound B at an application rate of n g/ha or at a concentration of n ppm and
$E$ is the efficacy when applying the active compounds A and B at application rates of m and n g/ha or at a concentration of m and n ppm, then $$E = X + Y - \frac{X \cdot Y}{100}$$

The efficacy is calculated in %. 0% is an efficacy which corresponds to that of the control, whereas an efficacy of 100% means that no infections occur.

If the actual activity exceeds the calculated value, then the activity of the combination is superadditive, i.e. a synergistic effect exists. In this case, the efficacy which was actually observed must be greater than the value for the expected efficacy (E) calculated from the abovementioned formula.

USE EXAMPLES

Example 1

| Pest: | *Aphis gossypii* |
|---|---|
| Crop: | Courgettes |

The spray liquor (1000 l of water/ha) comprising the active compound(s) was applied using a knapsack sprayer operated with compressed air. 4 spray applications were carried out at intervals of 9–13 days. The plot size was 12 m$^2$. The effect on the aphids was determined 7, 16 and 29 days after the last application (start of the infestation after the 2$^{nd}$ treatment) by counting the animals which were still alive/leaf (10 leaves/plot) and calculating the efficacy by the method of Abbott.

| Active compounds | Concentration % active compound | Efficacy % Abbott | | |
|---|---|---|---|---|
| | | 7* | 16* | 29* |
| 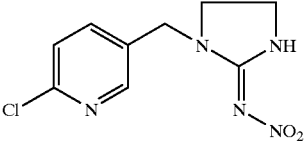 (IIa) | 0.015 | 100 | 89 | 33 |
| 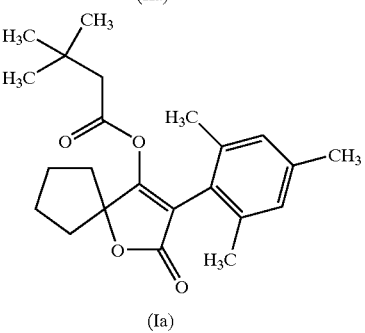 (Ia) | 0.0144 | 0 | 0 | 0 |
| IIa + Ia | 0.0075 + 0.0072 | 67 | 100 | 67 |

*Days after the last treatment

Example 2

| Pest: | *Bemisia tabaci* |
|---|---|
| Crop: | Cotton |

The spray liquor (1000 l of water/ha) comprising the active compound(s) was applied using a knapsack sprayer operated by pressurized air. The plot size was 19 m². The effect was evaluated 7, 10 and 14 days after the application by determining the number of larvae still alive on the leaf undersurface (10 leaves/plot) and calculating the efficacy by the method of Abbott.

| Active compounds | Dose kg of active compound/ha | Efficacy % Abbott | | |
|---|---|---|---|---|
| | | 7* | 10* | 14* |
| 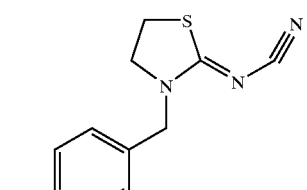 (IIk) | 0.096 | 86 | 61 | 68 |
| 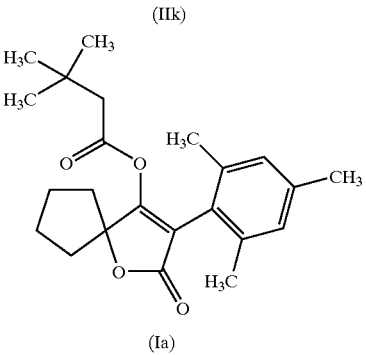 (Ia) | 0.0096 | 49 | 87 | 78 |
| IIk + Ia | 0.048 + 0.048 | 100 | 93 | 93 |

*Days after the last treatment

Example 3

| Bemisia test | |
|---|---|
| Solvent: | 7.5 parts by weight of dimethylformamide |
| Emulsifier: | 2.5 parts by weight of alkylaryl polyglycol ether |

To produce a suitable preparation of active compound, 1 part by weight of active compound is mixed with the stated amounts of solvent and emulsifier, and the concentrate is diluted with water to the desired concentrations.

Cotton plants (*Gossypium hirsutum*) which are infested by eggs, larvae and puparia of the white fly *Bemisia tabaci* are dipped into a preparation of active compound of the desired concentration.

After the desired period of time, the kill in % is determined. 100% means that all animals have been killed; 0% means that none of the animals have been killed.

| Active compounds | Active compound concentration in ppm | Kill in % after 10$^d$ | |
|---|---|---|---|
| Ex. (Ia) | 4 | 0 | |
| Ex. (IIa) | 4 | 0 | |
| Ex. (Ia) + Ex. (IIa) (1:1) | 4 + 4 | found.* | calc.** |
| | | 100 | 0 |

What is claimed is:

1. A composition for controlling pests, comprising a synergistically effective mixture of:
   (a) a compound of the Formula (Ia)

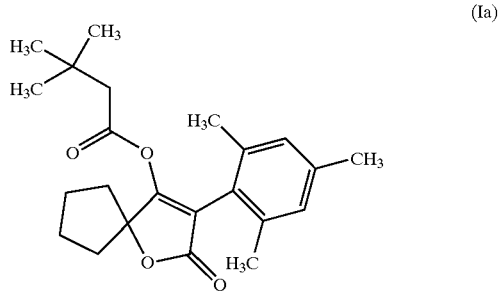

and
   (b) one or more agonists and/or antagonists of nicotinic acetylcholine receptors, wherein said agonist and/or antagonist of the nicotinic acetylcholine receptors is a compound of the Formula (II 1)

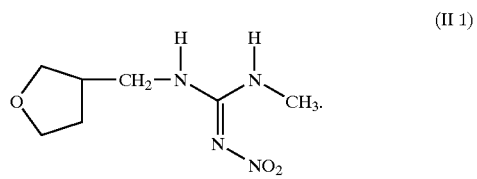

2. The composition according to claim 1 wherein said pests are selected from the group consisting of insect pests, acarid pests and combinations thereof.

3. A composition according to claim 1, comprising the compound of the Formula (Ia) and the compound of the Formula II 1 in a ratio of from 1:100 to 100:1.

4. A method of controlling pests, comprising the step of applying a synergistically effective mixture comprising a compound of the Formula (Ia) according to claim 1 and at least one compound of the Formula II 1 according to claim 1 to pests and/or their habitats.

5. The method of claim 4 wherein the pests are selected from the group consisting of insect pests, acarid pests and combinations thereof.

6. A process for preparing pesticides, comprising the step of mixing:
   (a) a synergistically effective mixture comprising a compound of the Formula (Ia) according to claim 1 and a compound of the Formulae II 1 according to claim 1, with
   (b) one or more extenders and/or surfactants.

* * * * *